(12) United States Patent
Borkum et al.

(10) Patent No.: US 10,933,251 B1
(45) Date of Patent: Mar. 2, 2021

(54) SYSTEM FOR NONINVASIVE PULSED MAGNETIC INDUCTION HEATING OF ACUPOINTS FOR THE NEUROREHABILITATION OF STROKE AND BRAIN INJURY, AND FOR THE PREVENTION AND TREATMENT OF DEMENTIA, AGE-RELATED COGNITIVE DECLINE, AND DEPRESSION

(71) Applicants: Jonathan M Borkum, Orono, ME (US); Mohsen Shahinpoor, Bangor, ME (US)

(72) Inventors: Jonathan M Borkum, Orono, ME (US); Mohsen Shahinpoor, Bangor, ME (US)

(*) Notice: Subject to any disclaimer, the term of this patent is extended or adjusted under 35 U.S.C. 154(b) by 0 days.

(21) Appl. No.: 16/903,808

(22) Filed: Jun. 17, 2020

(51) Int. Cl.
| A61N 2/02 | (2006.01) |
| A61N 2/10 | (2006.01) |
| A61B 5/0532 | (2021.01) |
| A61H 39/06 | (2006.01) |
| A61H 39/08 | (2006.01) |
| A61K 41/00 | (2020.01) |
| A61N 1/40 | (2006.01) |
| A61M 37/00 | (2006.01) |
| A61N 2/00 | (2006.01) |

(52) U.S. Cl.
CPC .......... *A61N 1/406* (2013.01); *A61H 39/06* (2013.01); *A61H 39/086* (2013.01); *A61K 41/0052* (2013.01); *A61M 37/0069* (2013.01); *A61M 2202/064* (2013.01); *A61N 2/004* (2013.01); *A61N 2/02* (2013.01)

(58) Field of Classification Search
CPC .... A61H 2201/0207; A61H 2201/0221; A61H 2201/5005; A61N 1/3787; A61N 2/02; A61N 1/40; A61N 1/0534; A61N 2/00; A61N 1/0536
See application file for complete search history.

(56) References Cited

U.S. PATENT DOCUMENTS

| 4,262,672 A | 4/1981 | Kief |
| 4,269,199 A | 5/1981 | Armitage |
(Continued)

FOREIGN PATENT DOCUMENTS

WO  PCT/US2014/024430    12/2014

OTHER PUBLICATIONS

Lu DP, Lu GP, Gabriel PL. Comparing the clinical effect of five varying locations of LI.4 acupoint. Acupunct Electrother Res. 2008;33(3-4):135-143.
(Continued)

*Primary Examiner* — Christine H Matthews
*Assistant Examiner* — Joshua Daryl D Lannu
(74) *Attorney, Agent, or Firm* — V Gerald Grafe

(57) ABSTRACT

Systems and devices for pulsed heating of the ST36 acupoint and/or other acupoint(s) by noninvasive transcutaneous magnetic induction heating towards (1) ameliorating cognitive impairment arising, for example, from head-injury, stroke, and neurodegenerative diseases such as Alzheimer's; (2) helping to prevent neurodegenerative diseases; (3) preventing and treating age-related cognitive decline; and (4) preventing and treating depression manifesting, for example, as Major Depressive Disorder, Dysthymic Disorder, or Adjustment Disorder with Depressed Mood.

20 Claims, 7 Drawing Sheets

(56) References Cited

U.S. PATENT DOCUMENTS

| | | | |
|---|---|---|---|
| 4,341,227 A | 7/1982 | Turner | |
| 4,448,198 A | 5/1984 | Turner | |
| 4,535,784 A | 8/1985 | Rohlicek et al. | |
| 4,553,546 A | 11/1985 | Javelle | |
| 4,621,642 A | 11/1986 | Chen | |
| 4,633,875 A | 1/1987 | Turner | |
| 5,010,897 A | 4/1991 | Leveen | |
| 6,347,251 B1 | 2/2002 | Deng | |
| 8,805,512 B1 | 8/2014 | Greiner et al. | |
| 8,832,834 B2 | 9/2014 | Lee | |
| 8,932,198 B1 | 1/2015 | You | |
| 8,996,125 B2 | 3/2015 | Greiner et al. | |
| 9,061,135 B1 | 6/2015 | Keller et al. | |
| 9,403,001 B2 | 8/2016 | Simon et al. | |
| 9,549,872 B2* | 1/2017 | Chen | A61N 1/3606 |
| 2004/0131543 A1* | 7/2004 | Wong | A61K 51/1255 424/1.11 |
| 2020/0188660 A1* | 6/2020 | Franke | A61N 1/406 |

OTHER PUBLICATIONS

Nam MH, Yin CS, Soh KS, Choi SH. Adult neurogenesis and acupuncture stimulation at ST36. J Acupunct Meridian Stud. 2011;4(3):153-158.

Niu X, Wen Z, Li X, Zhao W, Li X, Huang Y, et al. Fabrication of graphene and gold nanoparticle modified acupuncture needle electrode and its application in rutin analysis, Sensors and Actuators B: Chemical, 2018;255 Part 1:471-477.

GBD 2016 Dementia Collaborators. Global, regional, and national burden of Alzheimer's disease and other dementias, 1990-2016: a systematic analysis for the Global Burden of Disease Study 2016. Lancet Neurol. 2019;18:88-106.

Bherer L, Erickson KI, Liu-Ambrose T. A review of the effects of physical activity and exercise on cognitive and brain functions in older adults. Journal of Aging Research. 2013:657508.

Blondell SJ, Hammersley-Mather R, Lennert Veerman J. Does physical activity prevent cognitive decline and dementia? A systematic review and meta-analysis of longitudinal studies. BMC Public Health. 2014;14:510.

Heyn P, Abreu BC, Ottenbacher KJ. The effects of exercise training on elderly persons with cognitive impairment and dementia: a meta-analysis. Arch Phys Med Rehabil. 2004;85:1694-1704.

Wang R, Holsinger RMD. Exercise-induced brain-derived neurotrophic factor expression: Therapeutic implications for Alzheimer's dementia. Ageing Research Reviews. 2018;48:109-121.

Trigiani U, Hamel E. An endothelial link between the benefits of physical exercise and dementia. Journal of Cerebral Blood Flow and Metabolism. 2017;37:2649-2664.

Kim S-E, Ko I-G, Kim B-K, et al. Treadmill exercise prevents aging-induced failure of memory through an increase in neurogenesis and suppression of apoptosis in rat hippocampus. Experimental Gerontology. 2010;45:357-365.

Erickson KI, Voss MW, Shaurya Prakash R, et al. Exercise training increases size of hippocampus and improves memory. PNAS. 2011;108:3017-3022.

Greenberg PE, Fournier A-A, Sisitsky T, Pike CT, Kessler RC. The economic burden of adults with Major Depressive Disorder in the United States (2005 and 2010). J Clin Psychiatry. 2015;76:155-162.

Laursen TM, Musliner KL, Benros ME, Vestergaard M, Munk-Olsen T. Mortality and life expectancy in persons with severe unipolar depression. J Affect Disord. 2016;193:203-207.

Global Burden of Disease Study 2013 Colllaborators. Global, regional, and national incidence, prevalence, and years lived with disability for 301 acute and chronic diseases and injuries in 188 countries, 1990-2013: A systematic analysis for the Global Burden of Disease Study 2013. Lancet. 2015;386:743-800.

Morres ID, Hatzigeorgiadis A, Stathi A, Comoutos N, Arpin-Cribbie C, Krommidas C, Theodorakis Y. Aerobic exercise for adult patients with major depressive disorder in mental health services: a systematic review and meta-analysis. Depress Anxiety. 2019;36:39-53.

Belvederi Murri M, Ekkekakis P, Magagnoli M, Zampogna D, Cattedra S, Capobianco L, et al. Physical exercise in major depression: reducing the mortality gap while improving clinical outcomes. Frontiers in Psychiatry. 2019;9:762.

Tobi P, Kemp P, Schmidt E. Cohort differences in exercise adherence among primary care patients referred for mental health versus physical health conditions. Primary Health Care Research and Development. 2017;18:463-471.

Li P, Tjen-A-Looi SC, Cheng L, Liu D, Painovich J, Vinjamury S, Longhurst JC. Long-lasting reduction of blood pressure by electroacupuncture in patients with hypertension: randomized controlled trial. Med Acupunct. 2015;27:253-265.

Wu, W-Y., Chen, W-H, Hsieh C-L, Lin Y-W. Abundant expression and functional participation of TRPV1 at Zusanli acupoint (ST36) in mice: mechanosensitive TRPV1 as an "acupuncture responding channel." BMC Complement Altern Med. 2014;14:96.

Caterina, M. J. et al. The capsaicin receptor: a heat-activated ion channel in the pain pathway. Nature. 1997;389:816-824.

Wu Y-Y, Jiang Y-L, He X-F, Zhao X-Y, Shao X-M, Sun J, Shen Z, Shou S-Y, Wei J-J, Ye J-Y, Yan S-S, Fang J-Q. 5-HT in the dorsal raphe nucleus is involved in the effects of 100-Hz electroacupuncture on the pain-depression dyad in rats. Exp Ther Med. 2017;14:107-114.

Tao J, Chen B, Gao Y, Yang S, Huang J, Jiang X, Wu Y, Peng J, Hong Z, Chen L. Electroacupuncture enhances hippocampal NSCs proliferation in cerebral ischemia-reperfusion injured rats via activation of notch signaling pathway. Int J Neurosci. 2014;124:204-212.

Chavez LM, Huang S-S, MacDonald I, Lin J-G, Lee Y-C, Chen Y-H. Mechanisms of acupuncture therapy in ischemic stroke rehabilitation: a literature review of basic studies. Int J Mol Sci. 2017;18:2270.

Leung SB, Zhang H, Lau CW, Lin Z-X. Attenuation of blood pressure in spontaneously hypertensive rats by acupuncture was associated with reduction in oxidative stress and improvement from endothelial dysfunction. Chin Med. 2016;11:38.

Lee CH, Kim D-K, Yook T-H, Sasaki M, Kitamura N. Effectiveness of electroacupuncture at Zusanli (ST36) on the immunohistochemical density of enteroendocrine cells related to gastrointestinal function. J Acupunct Meridian Stud. 2012;5:63-71.

Yu C-C, Ma C-Y, Wang H, King L-H, Zhao Y, Shen F, Wu M. Effects of acupuncture on Alzheimer's disease: evidence from neuroimaging studies. Chin J Integr Med. 2018. DOI: 10.1007/s11655-018-2993-3.

Nam M-H, Ahn KS, Choi S-H. Acupuncture stimulation induces neurogenesis in adult brain. Int Rev Neurobiol. 2013;111:67-90.

Tong T, Pei C, Chen J, Lv Q, Zhang F, Chen g Z. Efficacy of acupuncture therapy for chemotherapy-related cognitive impairment in breast cancer patients. Med Sci Monit. 2018;24:2919-2927.

Zhang Q, Li Y-N, Guo Y-Y, Yin C=P, Gao F, Xin X, Huo S-P, Wang X-L, Wang Q-J. Effects of preconditioning of electro-acupuncture on postoperative cognitive dysfunction in elderly: A prospective, randomized, controlled trial. Medicine. 2017;96:26(e7375)

Huang L-P, Zhou S, Lu Z, Tian Q, Li X, Cao L-J, Yu J-h, Wang H. Bilateral effect of unilateral electroacupuncture on muscle strength. J Altern Complement Med. 2007;13:539-546.

Le J-J, Yi T, Qi L, Li J, Shao L, Dong J-C. Electroacupuncture regulate hypothalamic-pituitary-adrenal axis and enhance hippocampal serotonin system in a rat model of depression. Neuroscience Letters. 2016;615:66-71.

Sun H, Zhao H, Ma C, Bao F, Zhang J, Wang D-H, et al. Effects of electroacupuncture on depression and the production of glial cell line-derived neurotrophic factor compared with fluoxetine: a randomized controlled pilot study. Journal of Alternative and Complementary Medicine. 2013;19:733-739.

Wang H, Yang G, Wang S, Zheng X, Zhang W, Li Y. The most commonly treated acupuncture indications in the United States: a cross-sectional study. American Journal of Chinese Medicine. 2018;46:1387-1419.

Smith CA, Armour M, Lee MS, Wang LQ, Hay PJ. Acupuncture for depression. Cochrane Database Syst Rev. 2018;3:CD004046.

(56) References Cited

OTHER PUBLICATIONS

Youn J-I, Sung K-K, Song B-K, Kim M, Lee S. Effects of electroacupuncture therapy on post-stroke depression in patients with different degrees of motor function impairments: a pilot study. J Phys Ther Sci. 2013;25:725-728.

Li XB, Wang J, Xu AD, Huang JM, Meng LQ, Huang RY, Xu J. Clinical effects and safety of electroacupuncture for the treatment of post-stroke depression: a systematic review and meta-analysis of randomised controlled trials. Acupunct Med. 2018;36:284-293.

Simonsen EB. Contributions to the understanding of gait control. Dan Med J. 2011;61(4):B4823.

Ruiz-Muñoz M, Cuesta-Vargas AI. Electromyography and sonomyography analysis of the tibialis anterior: a cross sectional study. J Foot Ankle Res. 2014;7:11.

Scott LA, Murley GS, Wickham JB. The influence of footwear on the electromyographic activity of selected lower limb muscles during walking. J Electromyogr Kinesiol. 2012;22:1010-1016.

Shelburne KB, Torry MR, Pandy MG. Muscle, ligament, and joint-contact forces at the knee during walking. Med Sci Sports Exerc. 2005;37:1948-1956.

Chapple W. Proposed catalog of the neuroanatomy and the stratified anatomy for the 361 acupuncture points of 14 channels. J Acupunct Meridian Stud. 2013;6:270-274.

Deadman P, Al-Khafaji M, Kevin Baker K. Manual of acupuncture. Hove, East Sussex, England: Journal of Chinese Medicine Publications; 2007. (book cited as background information, copy not attached).

Firth J, Firth JA, Stubbs B, Vancampfort D, Schuch FitBit, Hallgren M, et al. Association between muscular strength and cognition in people with major depression and bipolar disorder and healthy controls. JAMA Psychiatry. 2018;75:740-746.

Veronese N, Stubbs B, Trevisan C, Bolzetta F, Rui MD, Solmi M, et al. What physical performance measures predict incident cognitive decline among intact older adults? A 4.4-year follow-up study. Exp Gerontol. 2016;80:110-118.

Fukumori N, Yamamoto Y, Takegami M, Yamazaki S, Onishi Y, Sekiguchi M, Fukuhara S. Association between hand-grip strength and depressive symptoms: Locomotive Syndrome and Health Outcomes in Aizu Cohort Study (LOHAS). Age Ageing. 2015;44:592-598.

Abraham TS, Chen M-L, Ma S-X. TRPV1 expression in acupuncture points: response to electroacupuncture stimulation. J Chem Neuroanat. 2011;41:129-136.

Kawakita K, Shinbara H, Imai K, Fukuda F, Yano T, Kuriyama K. How do acupuncture and moxibustion act? Focusing on the progress in Japanese acupuncture research. J Pharmacol Sci. 2006;100:443-459.

Caterina MJ, Rosen TA, Tominaga M, Brake AJ, Julius D. A capsaicin-receptor homologue with a high threshold for noxious heat. Nature. 1999;398:436-441.

Dewhirst MW, Viglianti BL, Lora-Michiels M, Hanson M, Hoopes PJ. Basic principles of thermal dosimetry and thermal thresholds for tissue damage from hyperthermia. Int J Hyperthermia. 2003;19:267-294.

Edwards RR, Fillingim RB. Effects of Age on Temporal Summation and Habituation of Thermal Pain: Clinical Relevance in Healthy Older and Younger Adults. J Pain. 2001;2:307-317.

Lee I-S, Lee Y-S, Park H-J, Lee H, Chae Y. Evaluation of phantom-based education system for acupuncture manipulation. PLoS One. 2015;10(2):e0117992.

Tan TT, Wang D, Huang JK, Zhou XM, Yuan X, Liang JP, et al. Modulatory effects of acupuncture on brain networks in mild cognitive impairment patients. Neural Regen Res. 2017;12:250-258.

Nishiwaki M, Takayama M, Yajima H, Nasu M, Park J, Kung J, Takakura N. A double-blind study on acupuncture sensations with Japanese style of acupuncture: comparison between penetrating and placebo needles. Evid Based Complement Alternat Med. 2018:8128147.

Yoo S-S, Lee W, Kim H. Pulsed application of focused ultrasound to the LI4 elicits deqi sensations: pilot study. Complement Ther Med. 2014;22:592-600.

\* cited by examiner

SYSTEM FOR NONINVASIVE PULSED MAGNETIC INDUCTION HEATING OF ACUPOINTS FOR THE NEUROREHABILITATION OF STROKE AND BRAIN INJURY, AND FOR THE PREVENTION AND TREATMENT OF DEMENTIA, AGE-RELATED COGNITIVE DECLINE, AND DEPRESSION

FIELD OF THE INVENTION

The invention is in the field of medical implants and acupuncture. It is broadly related to a non-invasive magnetic induction heating used in contact with mammalian skin over acupoints of interest in a mammalian body and methods of pulsed heating the acupoints of interest. More particularly, this invention relates to devices and methods for periodically raising the temperature of certain acupoints to between 44 and 50 degrees C. or so by pulsed alternating magnetic fields and magnetic induction heating of acupoints of interest.

BACKGROUND

There a number of scientific papers addressing ST36 acupuncture point stimulation towards ameliorating cognitive impairment arising, for example, from neurodegenerative diseases such as Alzheimer's, head-injury and stroke, and for preventing age-related cognitive decline. See, e.g., Min-Ho Nam, Chang ShikYin, Kwang-SupSoh and Seunghoon Choi, entitled "Adult Neurogenesis and Acupuncture Stimulation at ST36", Journal of Acupuncture and Meridian Studies, Volume 4, Issue 3, September 2011, Pages 153-158, for a review of the science.

There are several patents for devices providing steady heat to acupoints. U.S. Pat. No. 8,932,198 B1 describes use of a steady stream of water vapor, heated to between 38 and 50° C., to steadily warm certain acupuncture points to treat sleep disorders. Also, several U.S. patents and Chinese patents describe acupuncture devices that heat an acupuncture point, invasively or noninvasively, using microwave radiation. For example, U.S. Pat. No. 4,621,642 consists of a central metal bar that functions as a microwave antenna and a surrounding shield, insulated from the antenna. The apparatus, connected to a microwave generator, is placed in contact with the skin above an acupuncture point to heat it. In U.S. Pat. No. 6,347,251 B1, an acupuncture needle, which is the microwave antenna, is surrounded by a circular array of needles. The entire apparatus is inserted into an acupuncture point. No specific applications for the apparatus are designated.

U.S. Pat. No. 4,262,672 describes an acupuncture needle and surrounding conductor to electrically stimulate acupuncture points to achieve an analgesic effect. The authors note that if a soft ferrite tip were placed in the primary winding it would heat up, thermally stimulating the acupuncture point. Chinese Patent CN 2863098Y describes acupuncture needles with electrothermal properties to heat acupuncture points. In neither case is magnetic induction used to directly heat the tissues themselves.

U.S. Pat. No. 9,549,872 issued to Chen, et. al. on January 2017, entitled "Chronic electroaccupuncture [sic] using implanted electrodes" discusses certain embodiments which are directed to methods of treating diabetes, obesity, eating disorders, and gastrointestinal problems using chronically or permanently fully implanted electrodes. In certain aspects a stimulation lead is implanted proximally to an acupoint in the stomach (ST) meridian, which may include ST36, the stimulation lead being coupled to an implantable signal generator; and stimulating the acupoints using the signal generator to treat the metabolic disease. Although the primary intent is electro-acupuncture, the claims include magnetic or microwave stimulation of the electrodes to heat them, thermally stimulating the surrounding tissue. The heat would apparently be steady, be by means of chronically or permanently implanted electrodes and, again, the device is taught as used for treating eating disorders, gastrointestinal problems, and metabolic diseases such as diabetes and obesity.

A number of Chinese and Korean patents, and a few U.S. patents, use LEDs to deliver steady or pulsed infrared light to acupuncture points. For example, U.S. Pat. No. 4,553,546, issued Nov. 19, 1985, uses an 860 nm diode, with a pulse repetition interval of 1.720 or 0.860 msec., placed on the skin above an acupuncture point, to stimulate it. U.S. Pat. No. 4,535,784, issued Aug. 20, 1985, describes placing LEDs on the skin above an acupuncture point to irradiate it with visible or infrared light. U.S. Pat. No. 9,061,135 B1, issued Jun. 23, 2015, describes a similar device for treating chronic pain.

U.S. Pat. No. 8,996,125 B2 describes a self-contained implanted system for electrical stimulation of certain acupuncture points to treat cardiovascular disease. A second United States patent was subsequently issued for this device, for treating hypertension (patent number U.S. Pat. No. 8,805,512 B1). The device allows for an external electromagnetic field as a remote control for adjusting the stimulation parameters generated by the implanted device. The stimulation used in this device is purely electric. Thermal stimulation is not employed. An international patent application was filed for essentially the same device (number PCT/US2014/024430, filed Mar. 12, 2013 in the U.S. and Mar. 12, 2014 internationally).

U.S. Pat. No. 9,403,001 B2 includes the use of externally applied magnetic fields to noninvasively modulate activity in a cervical branch of the vagus nerve to treat functional gastrointestinal disorders. The role of the magnetic field is to directly modulate the electrical functioning of the nerve. Heat and acupuncture points are not involved.

There are also a number of Chinese patents addressing the same. Chinese Patent CN105148398A is entitled "Electroacupuncture needle therapeutic instrument for treating brain-derived diseases." This invention "relates to an electroacupuncture needle therapeutic instrument for treating brain-derived diseases and belongs to the medical apparatus and instrument field. With the electroacupuncture needle therapeutic instrument of the invention adopted, a plurality of acupuncture points can be treated simultaneously, the burden of the head of a patient can be decreased, and an excellent stimulating effect can be realized. According to the therapeutic instrument of the invention, an insulating elastic hat is provided with fixing belts which are used for fixing the insulating elastic hat on the head of the patient. The insulating elastic hat is divided into nine regions according to the parietal region, the pre-parietal region, the frontal area, the occipital region, the suboccipital region, the temporal region, the nuchal region, the prefrontal region and the post-parietal region of scalp points. Electroacupuncture needles are arranged in each region of the insulating elastic hat. The electroacupuncture needles are circular-ring-shaped electrodes. The inner round rings of electroacupuncture needle are filled with an electric conduction paste so that the circular-ring-shaped electrodes can act on the acupuncture points of the head of the patient after pulse current passes through the circular-ring-shaped electrodes. The electroacupuncture needle fixing rings penetrate the insulating elastic hat; and the sides of the electroacupuncture needle fixing rings, which are filled with the electric conduction paste, are located at the inner surface of the insulating elastic hat." Neither heating nor magnetic induction is used and the acupuncture points are restricted to those found on the head.

Chinese Patent CN1762509A presents an electrical pulse generator to electrically stimulate acupuncture points ST36 and LI4 at 2 Hz, 100 Hz, and at 2 Hz and 100 Hz alternately, in order to improve brain function.

Several patents relate to heating regions of the body to enhance blood flow, to restore temperature after hypothermic surgery or, especially, to selectively destroy tumors or other lesions. U.S. Pat. Nos. 4,341,227 and 4,633,875 describe systems for using electromagnetic radiation in the range of 900 MHz, from an applicator in contact with the body, to heat the underlying tissue. A sensor inserted into the tissue provides feedback for maintaining constant temperature. In U.S. Pat. No. 4,448,198, electromagnetic radiation is delivered selectively to a tissue at desired depth by using multiple applicators inserted into the body. Constructive interference of the emitted radiation is used to heat the tissue in order to selectively kill tumor cells.

In U.S. Pat. No. 4,269,199, an induction coil is positioned over the body for localized heating of a tumor. In U.S. Pat. No. 5,010,897, two induction coils are used, one on the anterior surface and one on the posterior surface of the body, heating the area between them by means of magnetic fields whose lines of force pass through the body.

There are also some patents related to internally heating medical implants by magnetic induction. U.S. Pat. No. 8,382,834 issued to Prescott in February 2013, entitled "Induction heater system for shape memory medical implants and method of activating shape memory medical implants within the mammalian body" presents a method of altering a medical implant having a shape memory portion. The device includes the use of a probe having a tip provided with an induction coil. The induction coil is electrically coupled to an induction power supply. The induction coil is inserted into the mammalian body. The power supply is activated at a suitable frequency to cause the induction coil to generate a magnetic field, wherein such magnetic field induces eddy currents in the shape memory portion of the implant which are sufficient to heat the shape memory portion of the implant to a phase transformation temperature to effect shape change of the implant.

None of the art suggests oscillatory magnetic inductive heating of acupoints for the purpose of preventing or treating cognitive impairment or for preventing or treating depression.

SUMMARY OF INVENTION

Systems and devices for pulsed heating of the ST36 acupoint and/or other acupoint(s) by noninvasive transcutaneous magnetic induction heating towards one or more of the following: (1) ameliorating cognitive impairment arising, for example, from head-injury, stroke, and neurodegenerative diseases such as Alzheimer's; (2) helping to prevent neurodegenerative diseases; (3) preventing and treating age-related cognitive decline; and (4) preventing and treating depression manifesting, for example, as Major Depressive Disorder, Dysthymic Disorder, or Adjustment Disorder with Depressed Mood. The heating system has a miniaturized tip equipped with an induction microcoil to periodically heat the acupoint(s) to temperatures between 44 and 50 degrees C. with a pulsation period of between 0.1 and 100 Hz, for example from 1 to 3 Hz, or 2 Hz. The acupoints can be considered as circular of about 2-4 mm in diameter. The induction coil can generate a magnetic field, wherein such magnetic field induces eddy currents in the conductive parts of the acupoint region and heats them up to, in turn and collectively, dynamically oscillate the temperature of the acupoint. Electrical lead connections, battery and the inductive heater micro-coils can be embedded in a brace (under-knee in the case of ST36 acupoint) to be close and almost in contact with the skin over the acupoint region. The acupoint region can be made highly electrically conductive (1) via electrically conductive gel, or (2) by carefully depositing gold particles on the acupoint by acupuncture needles and devices as, for example, can be performed by acupuncture.

Example embodiments of the present invention provide a method of treating a disorder comprising depositing a conductive substance on or into an acuregion, and periodically heating the acuregion using magnetic inductive heating of the conductive substance, wherein the acuregion is one or more of: ST36 (Zusanli), LI11 (Quchi), LI4 (Hegu), PC6 (Neiguan), and HT7 (Shenmen). In some embodiments, periodically heating the acuregion comprises heating the acuregion at a rate in the range from 0.1 Hz to 100 Hz.

In some embodiments, periodically heating the acuregion comprises heating the acuregion to a temperature in the range from 40 degrees C. to 50 degrees C. In some embodiments, periodically heating the acuregion comprises heating the acuregion at a rate in the range from 1.5 Hz to 2.5 Hz. In some embodiments, depositing a conductive substance on or into an acuregion comprises depositing a conductive gel on the acupoint region. In some embodiments, depositing a conductive substance on or into an acuregion comprises using hollow acupuncture needles to deposit microparticles, powders or network of a biocompatible conductor on the acupoint region. In some embodiments, the biocompatible conductor is gold. In some embodiments, the biocompatible conductor is graphene.

In some embodiments, the disorder is a neurodegenerative disease, a vascular dementia, a traumatic brain injury, an ischemic or hemorrhagic cerebrovascular accident, age-related cognitive decline, Major Depressive Disorder, Dysthymic Disorder, Adjustment Disorder with Depressed Mood, or other depressive disorder, or any combination thereof. In some embodiments, treating a disorder comprises an improvement in depression, or improvement in, or a reduction in the rate of decline in, one or more of: (a) short-term memory for verbal material, (b) verbal fluency, (c) short-term memory for visuospatial material, (d) visuospatial ability, (e) span of attention, (f) abstract reasoning, (g) cognitive processing speed.

DESCRIPTION OF INVENTION

Figure 1:
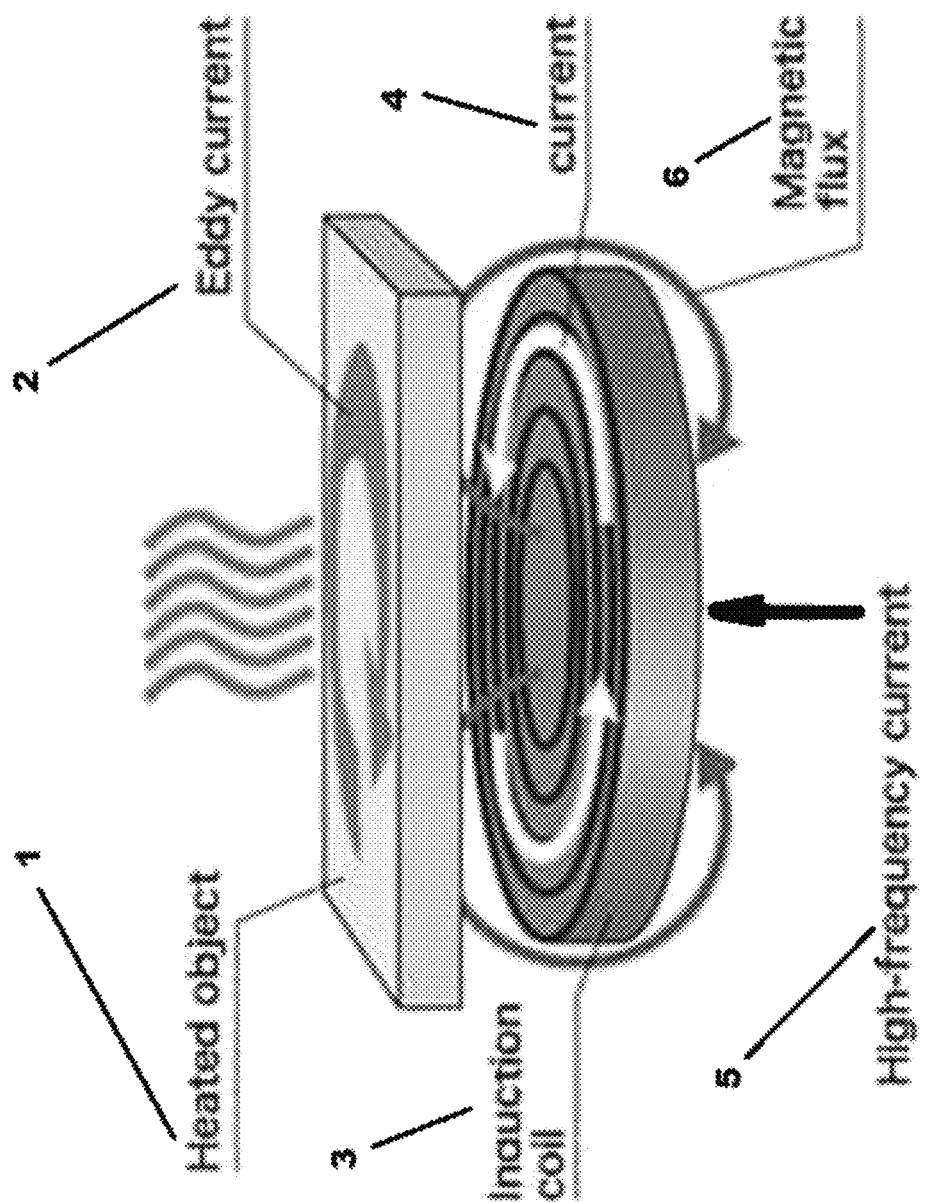
FIG. 1 is a schematic depiction of magnetic induction heating.

FIG. 1 depicts magnetic inductive heating in which a dynamical magnetic field induces eddy currents in a conductor (in this case, acupoint) close by and thus the eddy currents short out in the conductor and heat up the conductor by magnetic induction heating. Because the conductive part of the acupoint is shorted on itself, the eddy currents short out in the conductor and heat up the conductor by Joule heating due to remotely imposed magnetic induction. In FIG. 1, the various important parts of wirelessly heating the acupoint are shown. The heated ST36 acupoint with some conductive materials is denoted as number 1 while the eddy current shorted out in ST36 is shown in part number 2. Part number 3 displays the induction coil outside the body. Note the direction of induced current in part number 4 due to energizing high frequency current fed into the coil.

Figure 2:
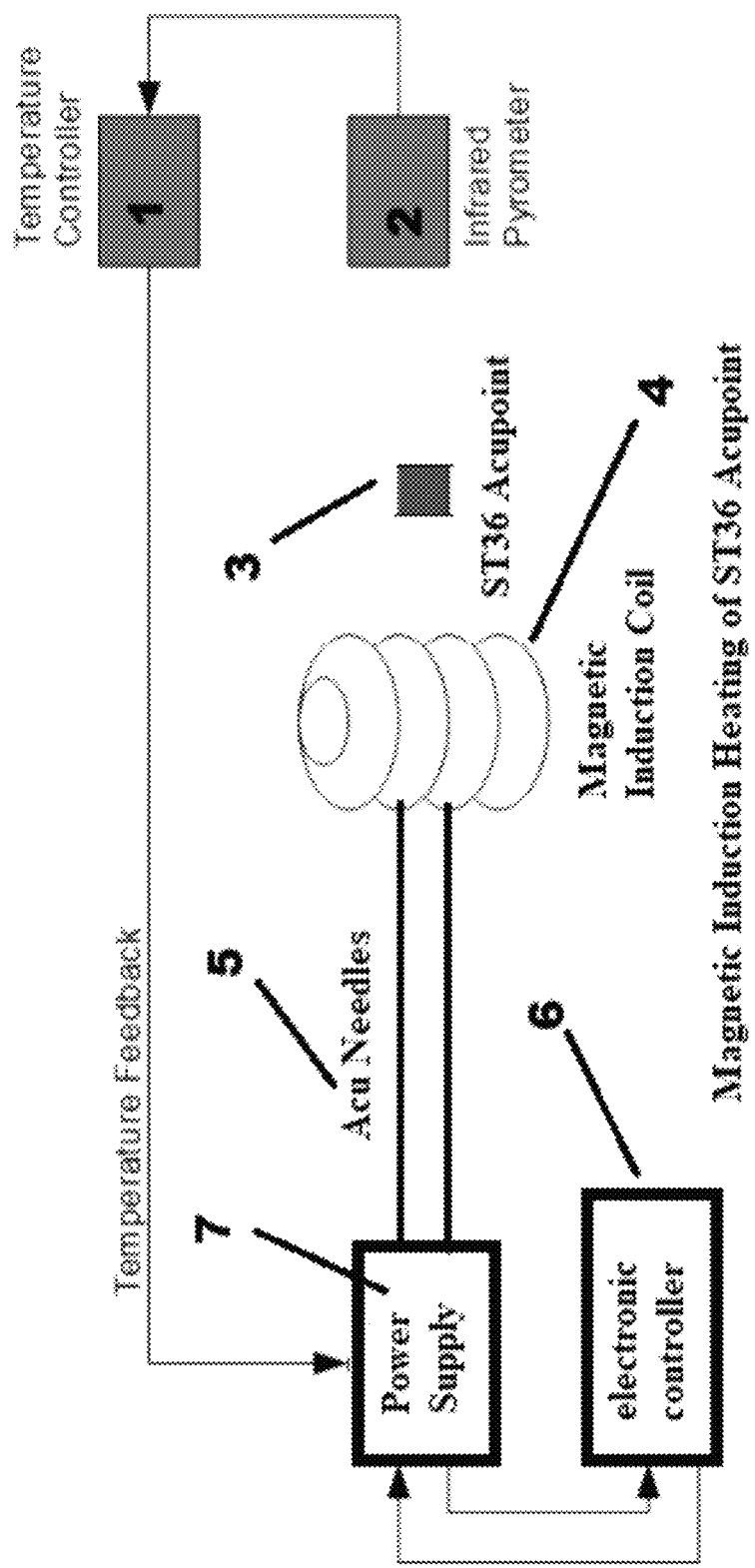
FIG. 2 is a schematic illustration of components of an example embodiment.

FIG. 2 depicts an example embodiment showing the arrangement of various components such as the power supply or battery, electronic controller to control the frequency of pulsation, the magnetic induction coils, the ST36 Zusanli acupoint, and the temperature controller and infrared pyrometer. FIG. 2 shows the electronic control of pulsed magnetic induction heating to produce alternating heating stimulation of acupuncture points. In FIG. 2, part 1 denotes the temperature controller which reads the temperature of ST36 by using an infrared pyrometer part number 2 and feeds that back to the power supply 7 which is controlled by the electronic controller part 6. The acuneedles part number 5 then energizes the magnetic induction coil part number 4 which remotely heats up the ST36 acupoint to the desired temperature (40-50 degrees C. or so).

Figure 3:
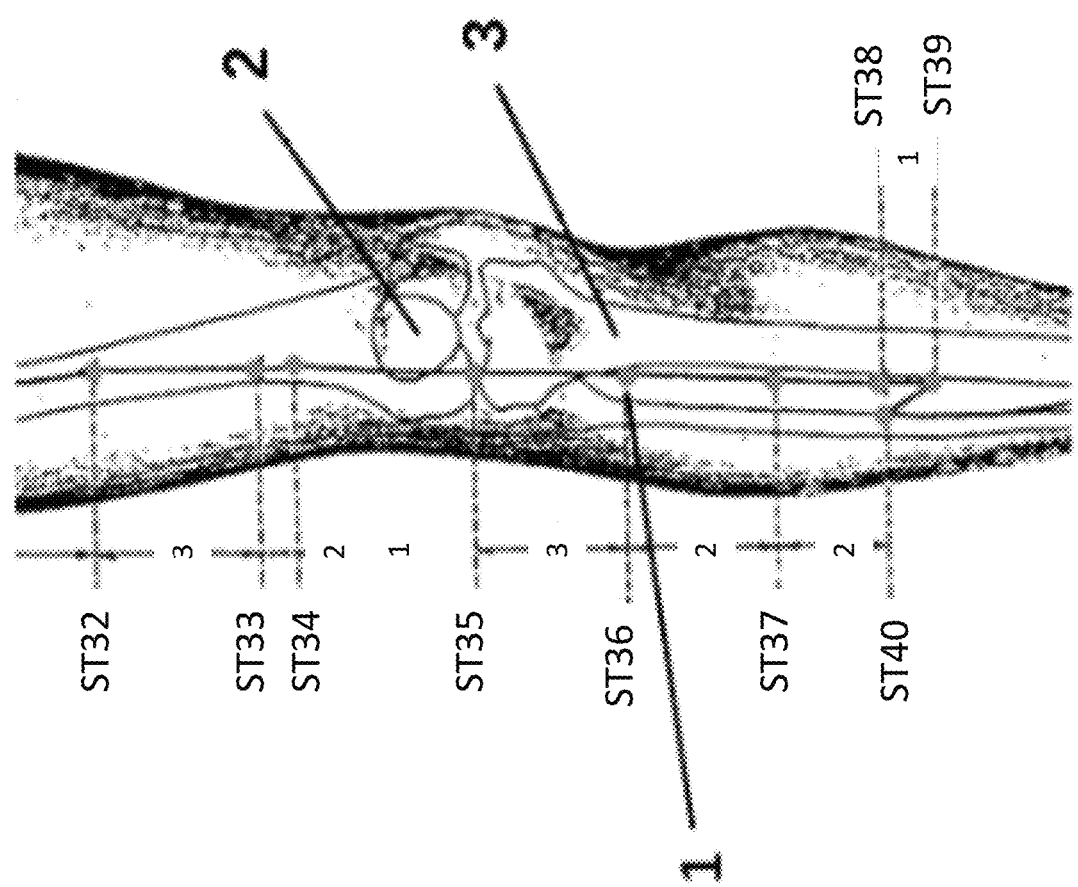
FIG. 3 is an illustration of the location of certain acupoints in the stomach meridian.

FIG. 3 depicts the location of certain acupoints in the stomach (ST) meridian. The ST36 Zusanli acupoint is located approximately 6 cm distal to the depression below the patella and approximately 2 cm lateral to the anterior ridge of the tibia.

Figure 4:
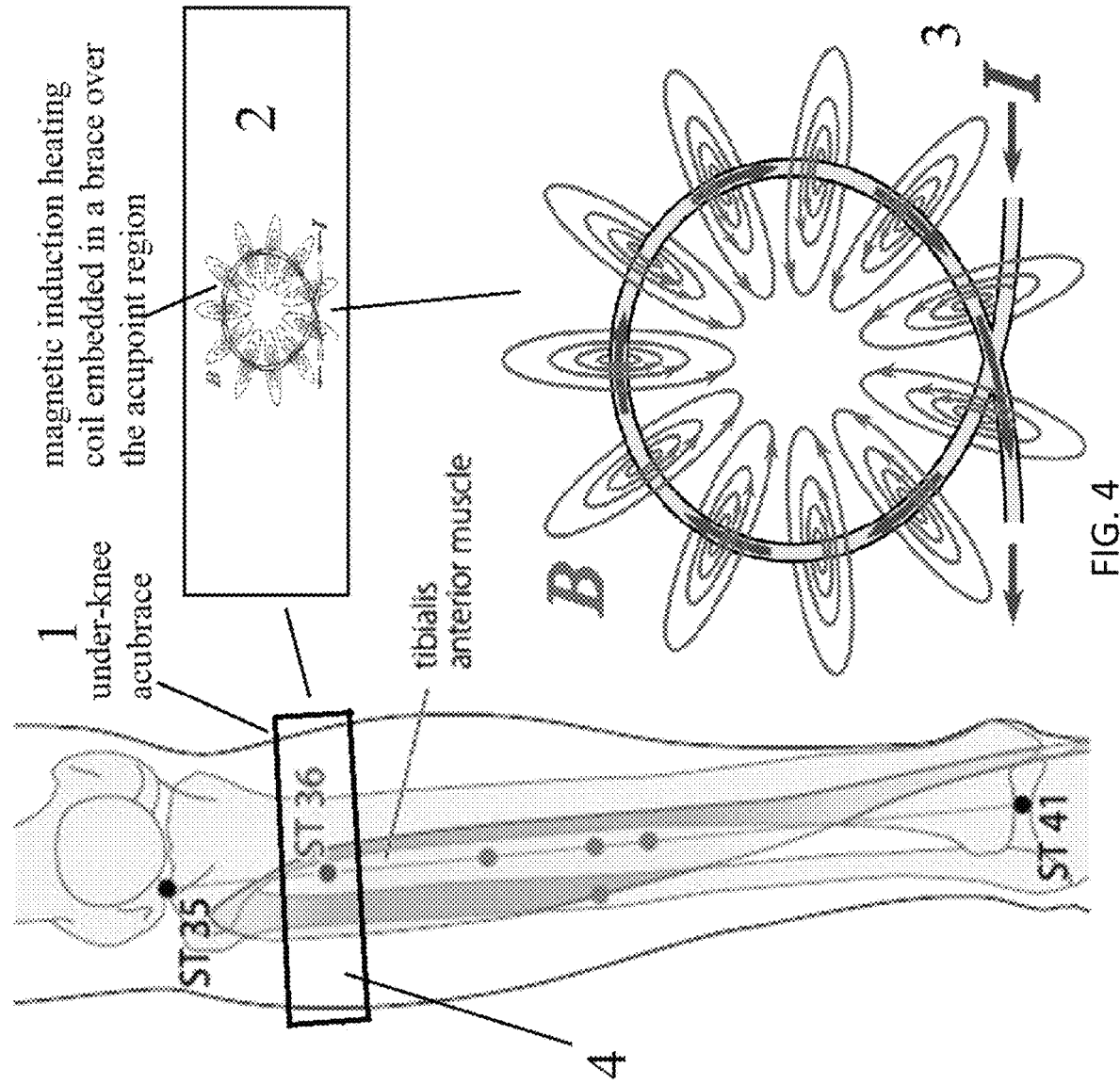
FIG. 4 is an illustration of a magnetic induction coil placed over an acuregion using a brace according to an example embodiment.

FIG. 4 depicts how the magnetic induction coil can be placed over the acuregion by a brace (below-knee in the case of ST36) to allow the magnetic induction to heat up the acupoint region of interest. Note in FIG. 4 that part number 1 displays the acupoint magnetic induction heating brace placed right under the knee over the acupoint region as shown in part 4. The magnetic induction heating brace 1 and 4 embed magnetic induction heating coil, as shown in part 2 in which an eddy current I as shown in part 3 is inducted for transcutaneously heating the ST 36 acupoint, as shown in part 3.

Figure 5:
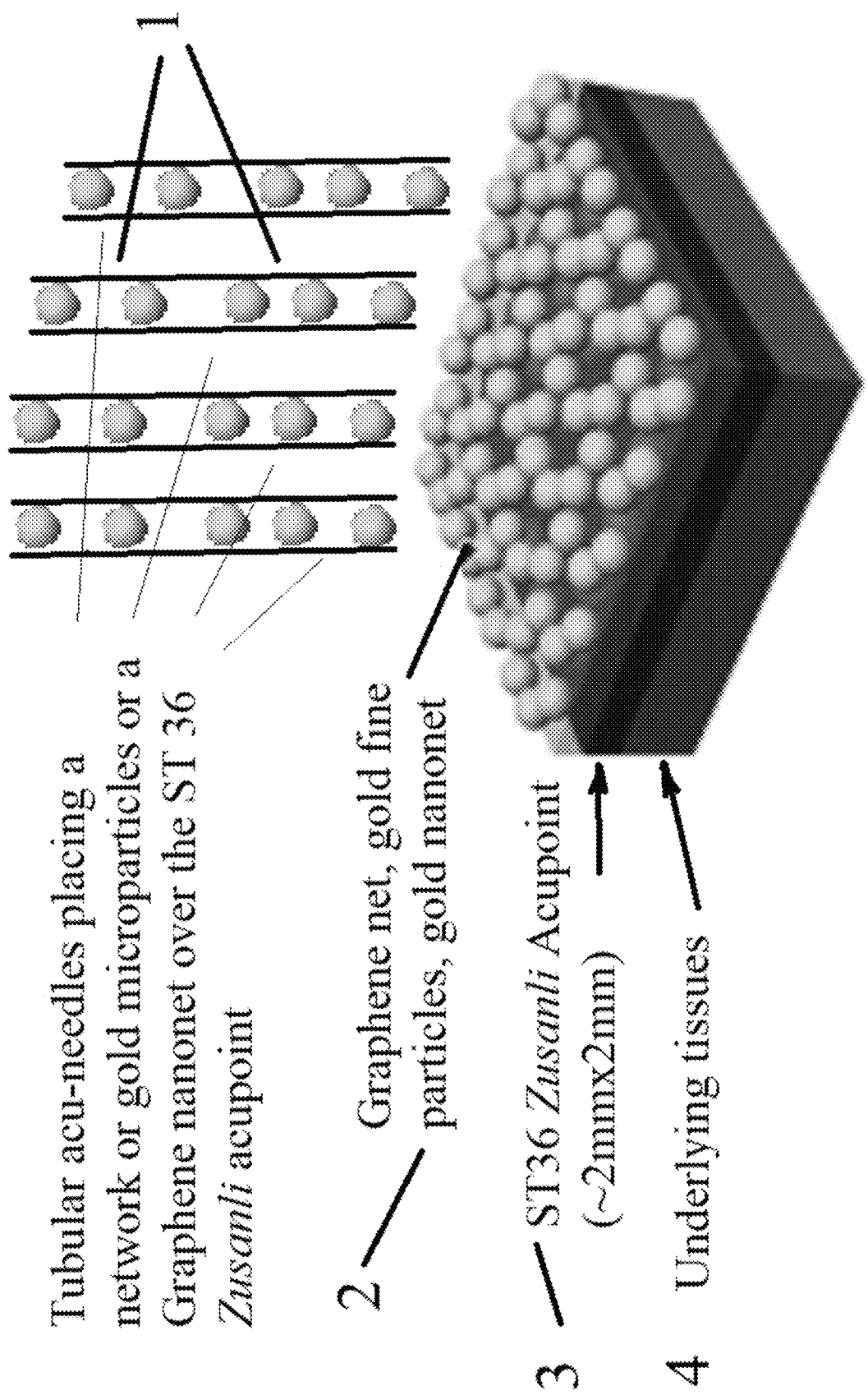
FIG. 5 is a schematic illustration of the placement of electrically conductive particles on an acupoint region.

FIG. 5 depicts how electrically conductive particles such as gold or nets such as graphene can be placed by acupuncture needles on the acupoint regions such as the Zusanli ST36 point. Note that in FIG. 5, microparticles of a conductive material such as platinum, gold or even highly conductive graphene (graphene net) as shown in part 2 in the figure are deposited through tubular acuneedles as shown in part number 2 right on the ST36 acuregion shown in part 3 located above the surrounding tissues shown in part number 4. Graphene nets and gold nanoparticles can be realized according to the teaching of Xueliang Niu, Zuorui Wen, Xiaobao Li, Wenshu Zhao Xiaoyan Li, Yaqi Huang, Qiutong Li, Guangjiu Li, Wei Sun, "Fabrication of graphene and gold nanoparticle modified acupuncture needle electrode and its application in rutin analysis", Sensors and Actuators B: Chemical, Volume 255, Part 1, February 2018, Pages 471-477, which is incorporated herein by reference.

Figure 6:
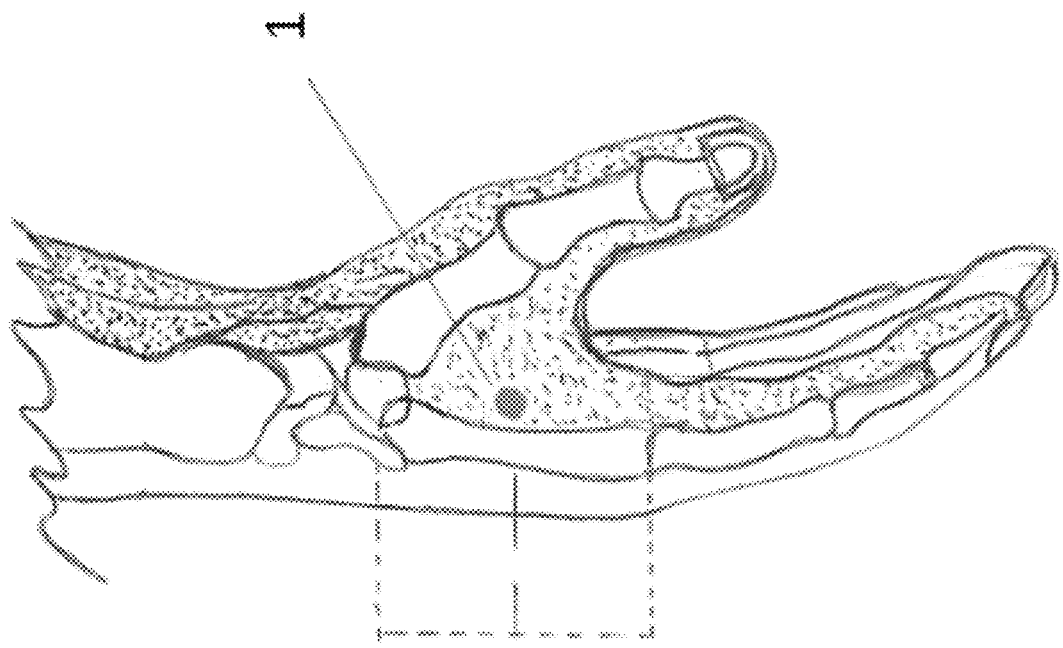

FIG. 6 illustrates the location of the LI4 Hegu acupuncture point, part 1, located in the adductor pollicis muscle at the highest point of the web space between the thumb and index finger.

Figure 7:
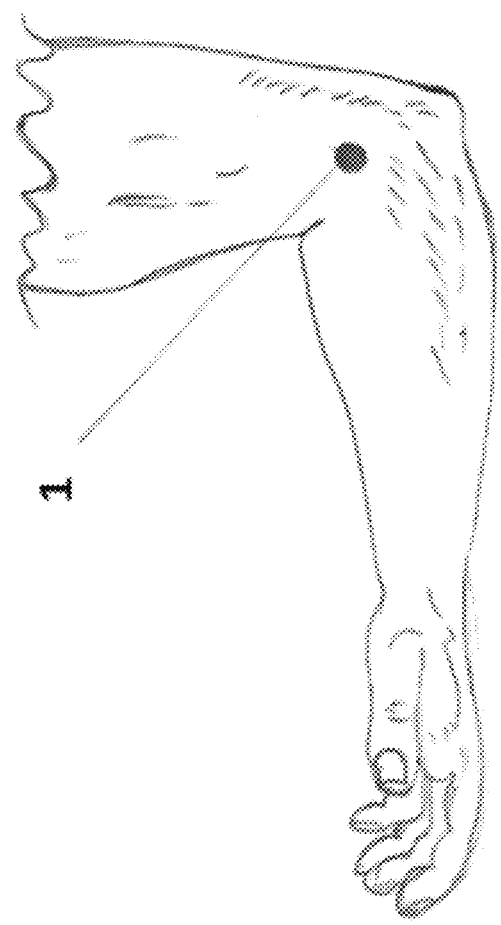
FIGS. 6-9 are illustrations of other acupoints useful with the present invention.

FIG. 7 illustrates the location of LI11 Quchi acupuncture point, part 1, located in the depression at the lateral end of the transverse cubital crease of the elbow, midway between the depression lateral to biceps brachii tendon and the lateral epicondyle of the humerus. This is the motor point of the extensor digitorum communis muscle.

Figure 8:
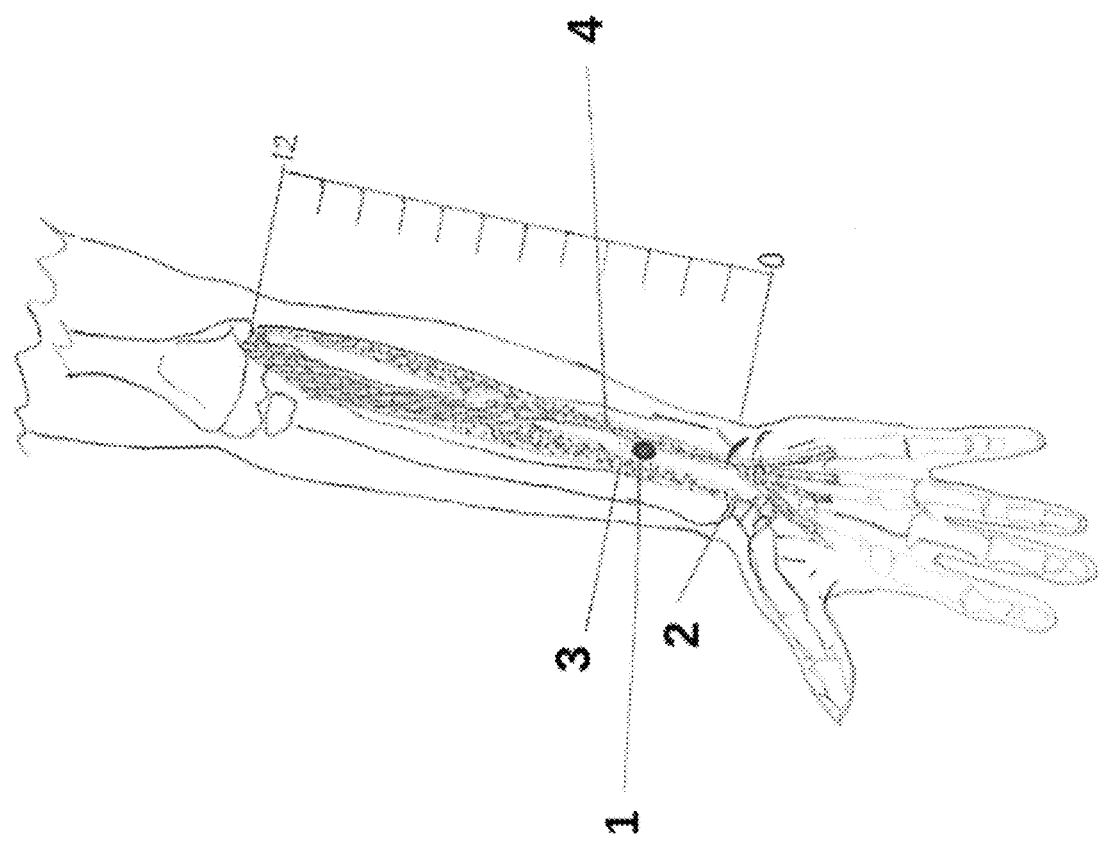

FIG. 8 illustrates the location of PC6 Neiguan acupuncture point, part 1, located at the center of the anterior forearm, between the tendons of the palmaris longus, part 4, and the flexor carpi radialis muscle, part 3, approximately 6.7 cm proximal to the crease of the wrist, part 2.

Figure 9:
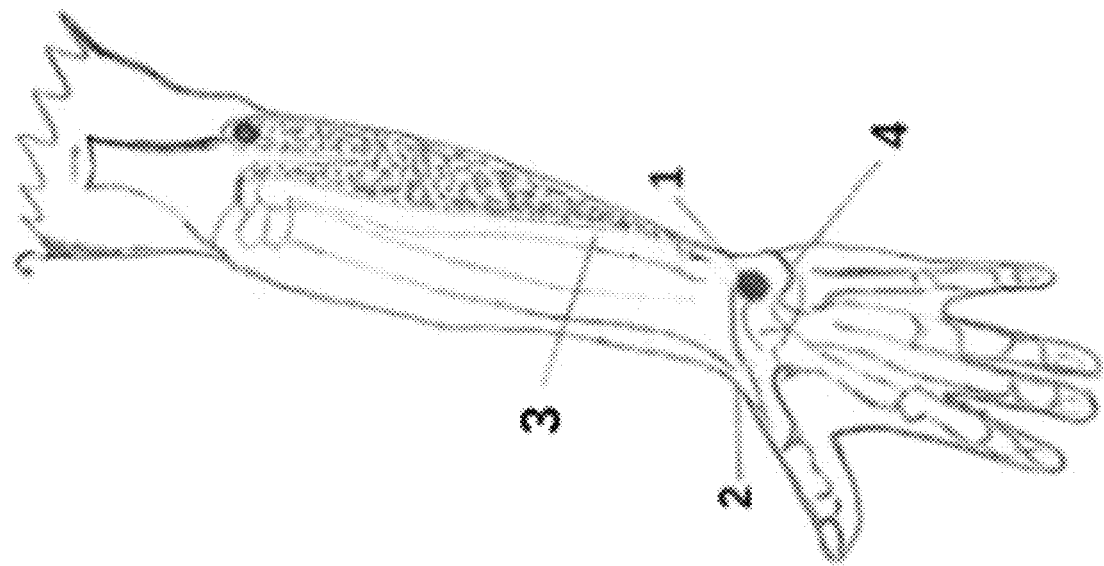

FIG. 9 illustrates the location of HT7 Shenmen acupuncture point, part 1, located at the medial end of the transverse crease of the wrist, part 2, between the ulna, part 3, and pisiform bone, part 4.

Problems Addressed by the Present Invention. Dementia from Alzheimer's disease and other causes currently affects 4 million Americans and 44 million people worldwide. Environmental and lifestyle factors have a large impact. In particular, physical exercise slows the rate of age-related cognitive decline, reduces the risk of developing dementia, and improves cognition in people who already have dementia. Physical exercise has considerable benefit for the brain by enhancing the production of brain-derived neurotrophic factor (BDNF), preserving and enhancing the brain's blood supply, protecting brain cells from apoptosis, increasing the birth of new brain cells (adult neurogenesis) and, in older adults, increasing the size of the hippocampus. However, even minimal physical exercise is unavailable to many people, and especially those most at risk of dementia, due to orthopedic problems, chronic pain, and movement disorders such as Parkinson's disease. Thus, there is a great need for other ways of achieving the same benefit.

Major Depressive Disorder alone affects 6.8% of American adults, entailing an estimated $210 billion in direct medical costs and lost workplace productivity, and accounts for approximately 50% of suicides. Even excluding suicide, Major Depressive Disorder is associated with a ten-year reduction in life expectancy. Worldwide, the prevalence of depression appears to have increased over the past thirty years.

Of note, physical exercise is an empirically supported treatment for Major Depressive Disorder; controlled clinical studies show moderate or large effect sizes, with little indication of publication bias. This is likely because of the favorable effects of physical exercise on the brain, noted above, and because exercise strengthens several homeostatic systems that are dysregulated in depression, including the hypothalamic-pituitary-adrenal axis, the sympathetic-parasympathetic autonomic balance, and regulation of the inflammatory response.

Here, too, however, exercise is often unavailable. The psychomotor slowing, fatigue, sleep disruption, and loss of motivation inherent in depression, as well as comorbidities such as chronic pain, make exercise difficult to achieve for depressed individuals. Thus, exercise programs show a high dropout rate among patients with Major Depressive Disorder. Again, there is a great need for other ways of achieving the same benefit.

For the beneficial adaptations of the brain and body to physical exercise to occur, the exercise must set in motion a sequence of signaling events. It is likely that some of these events are initiated by pressure-sensitive detectors that occur naturally in the muscles, overlying fascia, and nearby nerves and connective tissue. These physiological "exercise detectors" coincide with a number of acupuncture points.

In particular, the Zusanli or ST36 acupoint is located at the anterolateral lower leg, approximately 6 cm distal to the depression below the patella and approximately 2 cm lateral to the anterior ridge of the tibia (see FIG. 3). This acupoint includes subcutaneous connective tissue, a portion of the proximal anterior tibialis muscle, the overlying fascia, and a nerve trunk of the deep peroneal nerve.

This point contains an unusually high density, relative to a control, non-acupuncture point, of TRPV1, TRPV4, and ASIC3 cation channels, which transduce physical stimuli into biological signals. Among these, stimulation of the TRPV1 channels appears to be responsible for the effects of acupuncture. TRPV1 ion channels can be activated by mechanical or chemical stimulation, or by electricity, but first and foremost they are activated by heating to temperatures above 44° C.

Electroacupuncture stimulation, delivered through acupuncture needles inserted into this point, is generally just below motor threshold: 1 mA at 2 Hz for 20 minutes once a day. Stimulation of the correct point gives a deqi ("obtaining qi") sensation of paresthesias, heaviness, distension, or mild soreness.

Similar to exercise, stimulation of this acupuncture point appears to elicit a range of neuroprotective and neurorestorative processes. Thus, there is evidence that activation of the ST36 acupoint increases serotonin content of the dorsal raphe nucleus, raises serum levels of brain-derived neurotrophic factor (BDNF), stimulates hippocampal neurogenesis after ischemia, suppresses apoptosis of neurons, and may raise levels of activated endothelial nitric oxide synthase, (eNOS), calcitonin gene-related peptide (CGRP) and brain antioxidant defenses.

Stimulation of ST36 is part of traditional acupuncture protocols for stroke, Alzheimer's disease, and Parkinson's disease. In clinical studies it has been part of protocols showing effectiveness for reducing cognitive impairment from chemotherapy in breast cancer patients and postoperative cognitive dysfunction in the elderly.

In addition, stimulation of ST36 may facilitate brain recovery by protecting the blood vessel endothelium. Thus, activation of ST36 appears to treat hypertension by reducing oxidative and nitrosative stress in serum and blood vessel endothelium, reducing serum levels of angiotensin and the activity of oxidant-producing NADPH oxidase, and increasing the production and availability of nitric oxide. Moreover, electrical stimulation of ST36 on one leg strengthens the anterior tibialis muscle on both legs, implying an effect mediated by the central nervous system.

Similarly, stimulation of this acupuncture point appears to elicit other processes thought to be beneficial for depression. Thus, in an animal model of depression, acupuncture at ST36 and CV4 reduced hypothalamic-pituitary-adrenal axis over-activity and raised the concentration of serotonin and the serotonin 1a receptor in the hippocampus, changes that were correlated with an improvement in depression. In people, acupuncture at ST36 and DU20 raises serum levels of glial cell line-derived neurotrophic factor (GDNF) in concert with an improvement in depression.

Depression, in fact, is the second most common indication for acupuncture treatment in the US, slightly below low back pain. Acupuncture has received empirical support for the treatment of depression, although the clinical trial literature is still at an early stage in terms of methodological quality. In a randomized clinical trial it was as effective as 20 mg fluoxetine. Like exercise, acupuncture appears to have more rapid onset of action than fluoxetine. Thus, stimulation of ST36 is part of clinical studies showing effectiveness of acupuncture for depression, including post-stroke depression.

Moreover, depression is a risk factor for cardiovascular disease, which likely accounts for some of the excess mortality in individuals with Major Depressive Disorder. Thus, the beneficial effects on the endothelium from stimulating ST36, noted above, may be relevant to protecting depressed individuals from cardiovascular comorbidity.

Note that these physiological functions of ST36 closely resemble those of aerobic exercise such as walking. For example, the neurogenesis due to acupuncture at ST36, like that due to exercise, is specifically in the dentate gyrus of the hippocampus, where the new neurons allow the formation of new spatial maps—crucial to survival when one is walking in the jungle or forest.

This does not seem surprising, as the anterior tibialis muscle, where ST36 is located, participates in walking, tilting the foot upward (ankle dorsiflexion) while the leg is swinging forward so that the foot lands at the heel, thus reducing forces on the knee joint. Through eccentric contraction, the anterior tibialis also stabilizes the ankle, facilitating contact of the foot with the ground. On electromyography with surface electrodes, maximum firing of this muscle is during the contact phase, shortly after heel strike (i.e., at approximately 14% into the gait cycle). This is also a time when forces at the knee joint (the tibiofemoral capsule) are high. Thus, the pressure sensors at ST36, in the upper anterior tibialis, would seem well positioned to detect the forces associated with walking and communicate them to the brain.

Thus, the hypothesis is presented that many beneficial aspects of exercise (walking) are mediated through the central nervous system and can be replicated by communicating to the brain that one is walking. Moreover, this signal to the brain can be achieved by external stimulation of the ST36 acupuncture point. Oscillatory heat is used specifically because (1) the ST36 acupoint consists of ion channels that preferentially detect heat; (2) oscillation maximizes stimulation by preventing receptor fatigue; and (3) natural stimulation of the acupoint through exercise is oscillatory—for example, walking at normal speed involves tensing the anterior tibialis at approximately 2 Hz.

Of course, in the natural world, physical exercise and the attendant somatic stimulation rarely involves a single muscle in isolation. A number of other acupoints have been shown to enhance growth factor production, encourage adult neurogenesis, protect brain cells from apoptosis, and facilitate recovery from insults to the brain, as well as raise serotonin levels in the cortex and ameliorate depression.

These points include Hegu (LI4), Quchi (LI11), Neiguan (PC6), and Shenmen (HT7). Hegu is located in the adductor pollicis muscle, which governs the opposable thumb, bringing it into contact with the plane of the hand. Quchi is at the motor point of the extensor digitorum communis muscle, which extends the fingers and fires strongly to stabilize the wrist when gripping. Neiguan is towards the distal end of the flexor digitorum superficialis muscle, which flexes the fingers and wrist. Shenmen is in the distal anterior forearm, at the ulnar side of the wrist crease. It is located in the tendon of the flexor carpi ulnaris muscle.

All four muscles are active during use of the hands, and grasping in particular. Consistent with this, grip strength has been found in the scientific literature to correlate with cognitive performance across a range of domains in the present, and to predict reduced risk of future cognitive decline. Similarly, grip strength seems to correlate inversely with current depression and to predict future new-onset depression.

FIGS. 6, 7, 8, and 9 show the location of Hegu, Quichi, Neiguan, and Shenmen, respectively. These acupoints can be presumed to be circular, 2-4 mm in diameter. They can also be presumed to consist of TRPV1 ion channels. The present invention contemplates pulsed inductive heating of one or more of these points, in addition to or instead of ST36.

Temperature Parameters. The above noted acupuncture points are most likely made up of TRPV1 ion channels, which can be activated by mechanical stimulation (e.g., in acupuncture) or electricity (e.g., in electroacupuncture) but which are primarily detectors of noxious levels of heat. The stimulus-response curve of TRPV1 has been well mapped out. It begins generating excitatory currents at 44° C. This increases sharply at around 48° C. and reaches maximum at 52° C.

Tissue damage is not a risk with the parameters used in embodiments of the present invention. Skin would need to be exposed to 45° C. for 200 minutes continuously before sustaining tissue damage, and for muscle, tissue damage would not begin until 400 minutes of exposure. At 50° C. the corresponding parameters are 4 minutes for skin and 5 minutes for muscle. As the device would generate a temperature of 50° C. only in a brief, pulsed manner, the continuous exposure needed for localized necrosis would not obtain.

However, TRPV1 transduces noxious levels of heat, and by definition underlies heat pain. Heat pain begins after 6 seconds of continuous exposure at 45° C. and 2 seconds of exposure at 50° C. As half-peak current at an individual TRPV1 receptor is achieved in 35 msec., oscillation can activate the individual receptor while remaining below the pain threshold. Temporal summation at the spinal level begins with stimulation frequency greater than 0.33 Hz, and is somewhat greater in females and older adults. However, temporal summation is relatively constrained at 50° C., while at 47° C. there is habituation rather than summation.

Note that acupuncture itself needs to be mildly painful to be effective—the "de Qi" sensation is a mild, heavy, dull soreness at the site of needle insertion.

Anatomical Parameters. In traditional Chinese medicine, acupuncture needles are inserted at ST36 to a depth of between 0.92 and 4.60 cm. Superficial insertion (2-3 mm) is used as a control condition in acupuncture studies and has no effect. Insertion beyond 2.58 cm can entail damage to blood vessels and nerves so a depth of 1.25 cm should be safe while being in the effective range. The same depth is appropriate for LI11 and PC6. For LI4, a depth of 1.00 cm, and for HT7, a depth of 0.7 cm, is appropriate. All values are for adults.

ST36 is located approximately 6 cm distal to the depression below the patella and approximately 2 cm lateral to the anterior ridge of the tibia. LI4 is located at the highest point of the web space between the thumb and index finger. LI11 is located at the lateral (radial) corner of the crease of the elbow when the arm is bent at the elbow. PC6 is located at the center of the forearm (palmar side), between the tendons of the palmaris longus and the flexor carpi radialis muscles, approximately 6.7 cm proximal to the crease of the wrist. Acupuncture points are likely between 2 and 4 mm in diameter.

The depth of the acupuncture point depends on the body mass index of the person. Therefore, the depth of induction heating by the device can be adjustable. For ensuring safe operation, the device can be used specifically by acupuncture therapists and physical therapists who are already comfortable with needling techniques. For home use the device can be dispensed by a physical therapist after instructing the patient in its use, much as was done with TENS units for pain control. A timer can set stimulation to a preset duration, with a maximum duration of 30 minutes.

Typical stimulation parameters for electroacupuncture, in which a current is fed through an acupuncture needle, are 1 mA at 2 Hz for 20 minutes once a day. 2 Hz stimulation for 20 minutes will be modal for use of the unit.

The following references, each of which is incorporated herein by reference, can facilitate understanding of the invention.

Lu D P, Lu G P, Gabriel P L. Comparing the clinical effect of five varying locations of LI.4 acupoint. Acupunct Electrother Res. 2008; 33(3-4):135-143.

Nam M H, Yin C S, Soh K S, Choi S H. Adult neurogenesis and acupuncture stimulation at ST36. J Acupunct Meridian Stud. 2011; 4(3):153-158, Niu X, Wen Z, Li X, Zhao W, Li X, Huang Y, et al. Fabrication of graphene and gold nanoparticle modified acupuncture needle electrode and its application in rutin analysis, Sensors and Actuators B: Chemical, 2018; 255 Part 1:471-477.

GBD 2016 Dementia Collaborators. Global, regional, and national burden of Alzheimer's disease and other dementias, 1990-2016: a systematic analysis for the Global Burden of Disease Study 2016. Lancet Neurol. 2019; 18:88-106.

Bherer L, Erickson K I, Liu-Ambrose T. A review of the effects of physical activity and exercise on cognitive and brain functions in older adults. Journal of Aging Research. 2013:657508.

Blondell S J, Hammersley-Mather R, Lennert Veerman J. Does physical activity prevent cognitive decline and dementia? A systematic review and meta-analysis of longitudinal studies. BMC Public Health. 2014; 14:510.

Heyn P, Abreu B C, Ottenbacher K J. The effects of exercise training on elderly persons with cognitive impairment and dementia: a meta-analysis. Arch Phys Med Rehabil. 2004; 85:1694-1704.

Wang R, Holsinger R M D. Exercise-induced brain-derived neurotrophic factor expression: Therapeutic implications for Alzheimer's dementia. Ageing Research Reviews. 2018; 48:109-121.

Trigiani U, Hamel E. An endothelial link between the benefits of physical exercise and dementia. Journal of Cerebral Blood Flow and Metabolism. 2017; 37:2649-2664.

Kim S-E, Ko I-G, Kim B-K, et al. Treadmill exercise prevents aging-induced failure of memory through an increase in neurogenesis and suppression of apoptosis in rat hippocampus. Experimental Gerontology. 2010; 45:357-365.

Erickson K I, Voss M W, Shaurya Prakash R, et al. Exercise training increases size of hippocampus and improves memory. PNAS. 2011; 108:3017-3022.

Greenberg P E, Fournier A-A, Sisitsky T, Pike C T, Kessler R C. The economic burden of adults with Major Depressive Disorder in the United States (2005 and 2010). J Clin Psychiatry. 2015; 76:155-162.

Laursen T M, Musliner K L, Benros M E, Vestergaard M, Munk-Olsen T. Mortality and life expectancy in persons with severe unipolar depression. J Affect Disord. 2016; 193:203-207.

Global Burden of Disease Study 2013 Colllaborators. Global, regional, and national incidence, prevalence, and years lived with disability for 301 acute and chronic diseases and injuries in 188 countries, 1990-2013: A systematic analysis for the Global Burden of Disease Study 2013. Lancet. 2015; 386:743-800.

Morres I D, Hatzigeorgiadis A, Stathi A, Comoutos N, Arpin-Cribbie C, Krommidas C, Theodorakis Y. Aerobic exercise for adult patients with major depressive disorder in mental health services: a systematic review and meta-analysis. Depress Anxiety. 2019; 36:39-53.

Belvederi Murri M, Ekkekakis P, Magagnoli M, Zampogna D, Cattedra S, Capobianco L, et al. Physical exercise in major depression: reducing the mortality gap while improving clinical outcomes. Frontiers in Psychiatry. 2019; 9:762.

Tobi P, Kemp P, Schmidt E. Cohort differences in exercise adherence among primary care patients referred for mental health versus physical health conditions. Primary Health Care Research and Development. 2017; 18:463-471.

Li P, Tjen-A-Looi S C, Cheng L, Liu D, Painovich J, Vinjamury S, Longhurst J C. Long-lasting reduction of blood pressure by electroacupuncture in patients with hypertension: randomized controlled trial. Med Acupunct. 2015; 27:253-265.

Wu, W-Y., Chen, W-H, Hsieh C-L, Lin Y-W. Abundant expression and functional participation of TRPV1 at Zusanli acupoint (ST36) in mice: mechanosensitive TRPV1 as an "acupuncture responding channel." BMC Complement Altern Med. 2014; 14:96.

Caterina, M. J. et al. The capsaicin receptor: a heat-activated ion channel in the pain pathway. Nature. 1997; 389:816-824.

Wu Y-Y, Jiang Y-L, He X-F, Zhao X-Y, Shao X-M, Sun J, Shen Z, Shou S-Y, Wei J-J, Ye J-Y, Yan S-S, Fang J-Q. 5-HT in the dorsal raphe nucleus is involved in the effects of 100-Hz electro-acupuncture on the pain-depression dyad in rats. Exp Ther Med. 2017; 14:107-114.

Tao J, Chen B, Gao Y, Yang S, Huang J, Jiang X, Wu Y, Peng J, Hong Z, Chen L. Electroacupuncture enhances hippocampal NSCs proliferation in cerebral ischemia-reperfusion injured rats via activation of notch signaling pathway. Inti Neurosci. 2014; 124:204-212.

Chavez L M, Huang S-S, MacDonald I, Lin J-G, Lee Y-C, Chen Y-H. Mechanisms of acupuncture therapy in ischemic stroke rehabilitation: a literature review of basic studies. Int J Mol Sci. 2017; 18:2270.

Leung S B, Zhang H, Lau C W, Lin Z-X. Attenuation of blood pressure in spontaneously hypertensive rats by acupuncture was associated with reduction in oxidative stress and improvement from endothelial dysfunction. Chin Med. 2016; 11:38.

Lee C H, Kim D-K, Yook T-H, Sasaki M, Kitamura N. Effectiveness of electroacupuncture at Zusanli (ST36) on the immunohistochemical density of enteroendocrine cells related to gastrointestinal function. J Acupunct Meridian Stud. 2012; 5:63-71.

Yu C-C, MA C-Y, Wang H, King L-H, Zhao Y, Shen F, Wu M. Effects of acupuncture on Alzheimer's disease: evidence from neuroimaging studies. Chin J Integr Med. 2018. DOI: 10.1007/s11655-018-2993-3

Nam M-H, Ahn K S, Choi S-H. Acupuncture stimulation induces neurogenesis in adult brain. Int Rev Neurobiol. 2013; 111:67-90.

Tong T, Pei C, Chen J, Lv Q, Zhang F, Chen g Z. Efficacy of acupuncture therapy for chemotherapy-related cognitive impairment in breast cancer patients. Med Sci Monit. 2018; 24:2919-2927.

Zhang Q, Li Y-N, Guo Y-Y, Yin C=P, Gao F, Xin X, Huo S-P, Wang X-L, Wang Q-J. Effects of preconditioning of electro-acupuncture on postoperative cognitive dysfunction in elderly: A prospective, randomized, controlled trial. Medicine. 2017; 96:26(e7375)

Huang L-P, Zhou S, Lu Z, Tian Q, Li X, Cao L-J, Yu J-h, Wang H. Bilateral effect of unilateral electroacupuncture on muscle strength. J Altern Complement Med. 2007; 13:539-546.

Le J-J, Yi T, Qi L, Li J, Shao L, Dong J-C. Electroacupuncture regulate hypothalamic-pituitary-adrenal axis and enhance hippocampal serotonin system in a rat model of depression. Neuroscience Letters. 2016; 615:66-71.

Sun H, Zhao H, Ma C, Bao F, Zhang J, Wang D-H, et al. Effects of electroacupuncture on depression and the production of glial cell line-derived neurotrophic factor compared with fluoxetine: a randomized controlled pilot study. Journal of Alternative and Complementary Medicine. 2013; 19:733-739.

Wang H, Yang G, Wang S, Zheng X, Zhang W, Li Y. The most commonly treated acupuncture indications in the United States: a cross-sectional study. American Journal of Chinese Medicine. 2018; 46:1387-1419.

Smith C A, Armour M, Lee M S, Wang L O, Hay P J. Acupuncture for depression. Cochrane Database Syst Rev. 2018; 3:CD004046.

Youn J-I, Sung K-K, Song B-K, Kim M, Lee S. Effects of electro-acupuncture therapy on post-stroke depression in patients with different degrees of motor function impairments: a pilot study. J Phys Ther Sci. 2013; 25:725-728.

Li X B, Wang J, Xu A D, Huang J M, Meng L O, Huang R Y, Xu J. Clinical effects and safety of electroacupuncture for the treatment of post-stroke depression: a systematic review and meta-analysis of randomised controlled trials. Acupunct Med. 2018; 36:284-293.

Belvederi Murri M, Ekkekakis P, Magagnoli M, Zampogna D, Cattedra S, Capobianco L, et al. Physical exercise in major depression: reducing the mortality gap while improving clinical outcomes. Frontiers in Psychiatry. 2019; 9:762.

Simonsen E B. Contributions to the understanding of gait control. Dan Med J. 2011; 61(4):B4823

Ruiz-Muñoz M, Cuesta-Vargas A I. Electromyography and sonomyography analysis of the tibialis anterior: a cross sectional study. J Foot Ankle Res. 2014; 7:11.

Scott L A, Murley G S, Wickham J B. The influence of footwear on the electromyographic activity of selected lower limb muscles during walking. J Electromyogr Kinesiol. 2012; 22:1010-1016.

Shelburne K B, Torry M R, Pandy M G. Muscle, ligament, and joint-contact forces at the knee during walking. Med Sci Sports Exerc. 2005; 37:1948-1956.

Chapple W. Proposed catalog of the neuroanatomy and the stratified anatomy for the 361 acupuncture points of 14 channels. J Acupunct Meridian Stud. 2013; 6:270-274.

Deadman P, Al-Khafaji M, Kevin Baker K. Manual of acupuncture. Hove, East Sussex, England: Journal of Chinese Medicine Publications; 2007.

Firth J, Firth J A, Stubbs B, Vancampfort D, Schuch FitBit, Hallgren M, et al. Association between muscular strength and cognition in people with major depression and bipolar disorder and healthy controls. JAMA Psychiatry. 2018; 75:740-746.

Veronese N, Stubbs B, Trevisan C, Bolzetta F, Rui M D, Solmi M, et al. What physical performance measures predict incident cognitive decline among intact older adults? A 4.4-year follow-up study. Exp Gerontol. 2016; 80:110-118.

Fukumori N, Yamamoto Y, Takegami M, Yamazaki S, Onishi Y, Sekiguchi M, Fukuhara S. Association between hand-grip strength and depressive symptoms: Locomotive Syndrome and Health Outcomes in Aizu Cohort Study (LOHAS). Age Ageing. 2015; 44:592-598.

Abraham T S, Chen M-L, Ma S-X. TRPV1 expression in acupuncture points: response to electroacupuncture stimulation. J Chem Neuroanat. 2011; 41:129-136.

Kawakita K, Shinbara H, Imai K, Fukuda F, Yano T, Kuriyama K. How do acupuncture and moxibustion act? Focusing on the progress in Japanese acupuncture research. J Pharmacol Sci. 2006; 100:443-459.

Caterina M J, Rosen T A, Tominaga M, Brake A J, Julius D. A capsaicin-receptor homologue with a high threshold for noxious heat. Nature. 1999; 398:436-441.

Dewhirst M W, Viglianti B L, Lora-Michiels M, Hanson M, Hoopes P J. Basic principles of thermal dosimetry and thermal thresholds for tissue damage from hyperthermia. Int J Hyperthermia. 2003; 19:267-294.

Edwards R R, Fillingim R B. Effects of Age on Temporal Summation and Habituation of Thermal Pain: Clinical Relevance in Healthy Older and Younger Adults. J Pain. 2001; 2:307-317.

Lee I-S, Lee Y-S, Park H-J, Lee H, Chae Y. Evaluation of phantom-based education system for acupuncture manipulation. PLoS One. 2015; 10(2):e0117992.

Tan T T, Wang D, Huang J K, Zhou X M, Yuan X, Liang J P, et al. Modulatory effects of acupuncture on brain networks in mild cognitive impairment patients. Neural Regen Res. 2017; 12:250-258.

Nishiwaki M, Takayama M, Yajima H, Nasu M, Park J, Kung J, Takakura N. A double-blind study on acupuncture sensations with Japanese style of acupuncture: comparison between penetrating and placebo needles. Evid Based Complement Alternat Med. 2018:8128147.

Yoo S-S, Lee W, Kim H. Pulsed application of focused ultrasound to the LI4 elicits deqi sensations: pilot study. Complement Ther Med. 2014; 22:592-600.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of treating a disorder comprising depositing a conductive substance on or into an acuregion, and periodically heating the acuregion using magnetic inductive heating of the conductive substance, wherein the acuregion is one or more of: ST36 (Zusanli), LI11 (Quchi), LI4 (Hegu), PC6 (Neiguan), and HT7 (Shenmen), wherein the conductive substance comprises one or more of: an electrically conductive gel, gold particles, conductive microparticles, a conductive powder, a network of a biocompatible conductor, graphene, a graphene net, or platinum.

2. The method of claim 1, wherein periodically heating the acuregion comprises heating the acuregion at a rate in the range from 0.1 Hz to 100 Hz.

3. The method of claim 2, wherein periodically heating the acuregion comprises heating the acuregion to a temperature in the range from 40 degrees C. to 50 degrees C.

4. The method of claim 2, wherein periodically heating the acuregion comprises heating the acuregion at a rate in the range from 1.5 Hz to 2.5 Hz.

5. The method of claim 1, wherein periodically heating the acuregion comprises heating the acuregion to a temperature in the range from 40 degrees C. to 50 degrees C.

6. The method of claim 1, wherein depositing a conductive substance on or into an acuregion comprises using hollow acupuncture needles to deposit microparticles, powders, or a network of a biocompatible conductor on the acuregion.

7. The method of claim 6, wherein the biocompatible conductor is graphene.

8. The method of claim 1, wherein the disorder is a neurodegenerative disease.

9. The method of claim 8, wherein treating a disorder comprises an improvement in depression, or improvement in, or a reduction in the rate of decline in, one or more of: (a) short-term memory for verbal material, (b) verbal fluency, (c) short-term memory for visuospatial material, (d) visuospatial ability, (e) span of attention, (f) abstract reasoning, and (g) cognitive processing speed.

10. The method of claim 1, wherein the disorder is a vascular dementia.

11. The method of claim 10, wherein treating a disorder comprises an improvement in depression, or improvement in, or a reduction in the rate of decline in, one or more of: (a) short-term memory for verbal material, (b) verbal fluency, (c) short-term memory for visuospatial material, (d) visuospatial ability, (e) span of attention, (f) abstract reasoning, (g) cognitive processing speed.

12. The method of claim 1, wherein the disorder is a traumatic brain injury.

13. The method of claim 12, wherein treating a disorder comprises an improvement in depression, or improvement in, or a reduction in the rate of decline in, one or more of: (a) short-term memory for verbal material, (b) verbal fluency, (c) short-term memory for visuospatial material, (d) visuospatial ability, (e) span of attention, (f) abstract reasoning, and (g) cognitive processing speed.

14. The method of claim 1, wherein the disorder is an ischemic or hemorrhagic cerebrovascular accident.

15. The method of claim 14, wherein treating a disorder comprises an improvement in depression, or improvement in, or a reduction in the rate of decline in, one or more of: (a) short-term memory for verbal material, (b) verbal fluency, (c) short-term memory for visuospatial material, (d) visuospatial ability, (e) span of attention, (f) abstract reasoning, and (g) cognitive processing speed.

16. The method of claim 1, wherein the disorder is age-related cognitive decline.

17. The method of claim 16, wherein treating a disorder comprises an improvement in depression, or improvement in, or a reduction in the rate of decline in, one or more of: (a) short-term memory for verbal material, (b) verbal fluency, (c) short-term memory for visuospatial material, (d) visuospatial ability, (e) span of attention, (f) abstract reasoning, and (g) cognitive processing speed.

18. The method of claim 1, wherein the disorder is major depressive disorder, dysthymic disorder, adjustment disorder with depressed mood, or other depressive disorder.

19. A method of treating a disorder comprising depositing a conductive substance on or into an acuregion, and periodically heating the acuregion using magnetic inductive heating of the conductive substance, wherein the acuregion is one or more of: ST36 (Zusanli), LI11 (Quchi), LI4 (Hegu), PC6 (Neiguan), and HT7 (Shenmen), wherein depositing a conductive substance on or into an acuregion comprises depositing a conductive gel on the acuregion.

20. A method of treating a disorder comprising depositing a conductive substance on or into an acuregion, and periodically heating the acuregion using magnetic inductive heating of the conductive substance, wherein the acuregion is one or more of: ST36 (Zusanli), LI11 (Quchi), LI4 (Hegu), PC6 (Neiguan), and HT7 (Shenmen), wherein depositing a conductive substance on or into an acuregion comprises using hollow acupuncture needles to deposit microparticles, powders, or a network of a biocompatible conductor on the acuregion, wherein the biocompatible conductor is gold.

* * * * *